United States Patent

McGurk et al.

[11] Patent Number: 6,165,198
[45] Date of Patent: *Dec. 26, 2000

[54] EMBOLIC ELEMENTS AND METHODS AND APPARATUS FOR THEIR DELIVERY

[75] Inventors: Erin McGurk; Ronald Dieck, both of Palo Alto; William S. Tremulis, Redwood City, all of Calif.

[73] Assignee: Medtronic, Inc., Minneapolis, Minn.

[*] Notice: This patent is subject to a terminal disclaimer.

[21] Appl. No.: 08/849,678

[22] PCT Filed: Dec. 12, 1995

[86] PCT No.: PCT/US95/16022

§ 371 Date: Aug. 31, 1998

§ 102(e) Date: Aug. 31, 1998

[87] PCT Pub. No.: WO96/18343

PCT Pub. Date: Jun. 20, 1996

Related U.S. Application Data

[63] Continuation-in-part of application No. 08/355,142, Dec. 13, 1994, Pat. No. 5,690,671.

[51] Int. Cl.[7] .......................... A61M 29/00; A61B 17/00
[52] U.S. Cl. ................................. 606/200; 606/1
[58] Field of Search ................ 606/1, 191, 194, 606/195, 198, 32, 34, 200; 623/1, 12

[56] References Cited

U.S. PATENT DOCUMENTS

| | | |
|---|---|---|
| 3,868,956 | 3/1975 | Alfidi et al. . |
| 4,170,990 | 10/1979 | Baumgart et al. . |
| 4,503,569 | 3/1985 | Dotter . |
| 4,512,338 | 4/1985 | Balko et al. . |
| 4,739,768 | 4/1988 | Engelson . |
| 4,813,934 | 3/1989 | Engelson et al. . |
| 4,884,579 | 12/1989 | Engelson . |
| 4,950,258 | 8/1990 | Kawai et al. . |
| 4,994,069 | 2/1991 | Ritchart et al. . |
| 5,067,957 | 11/1991 | Jervis . |
| 5,108,407 | 4/1992 | Geremia et al. . |
| 5,108,420 | 4/1992 | Marks . |
| 5,109,867 | 5/1992 | Twyford, Jr. . |
| 5,122,136 | 6/1992 | Guglielmi et al. . |
| 5,217,484 | 6/1993 | Marks . |
| 5,226,911 | 7/1993 | Chee et al. . |
| 5,234,437 | 8/1993 | Sepetka . |
| 5,250,071 | 10/1993 | Palermo . |
| 5,261,916 | 11/1993 | Engelson . |
| 5,312,415 | 5/1994 | Palermo . |
| 5,624,461 | 4/1997 | Mariant . |

FOREIGN PATENT DOCUMENTS

| | | |
|---|---|---|
| 0 747 013 A1 | 12/1996 | European Pat. Off. . |
| 0 747 014 A1 | 12/1996 | European Pat. Off. . |
| 0 750 886 A1 | 1/1997 | European Pat. Off. . |
| 2 641 692 | 7/1990 | France . |
| WO 93/06884 | 4/1993 | WIPO . |
| WO 94/06503 | 3/1994 | WIPO . |
| WO 94/09705 | 5/1994 | WIPO . |
| WO 94/10936 | 5/1994 | WIPO . |
| WO 94/11051 | 5/1994 | WIPO . |
| WO 94/15534 | 7/1994 | WIPO . |

*Primary Examiner*—Michael Buiz
*Assistant Examiner*—William W. Lewis

[57] ABSTRACT

An embolic element comprises a filament composed of a shape memory material having an unexpanded coil configuration and an expanded random matrix configuration. The embolic element may be delivered to a blood vessel treatment site in its coiled configuration over a delivery wire through a guide catheter (44). Usually, the coiled embolic element will be disposed over a helical section of the delivery wire prior to release. In that way, proper positioning of the embolic element is then expanded to its enlarged configuration by heating or otherwise exposing to a temperature over the transition temperature of the shape memory material.

23 Claims, 5 Drawing Sheets

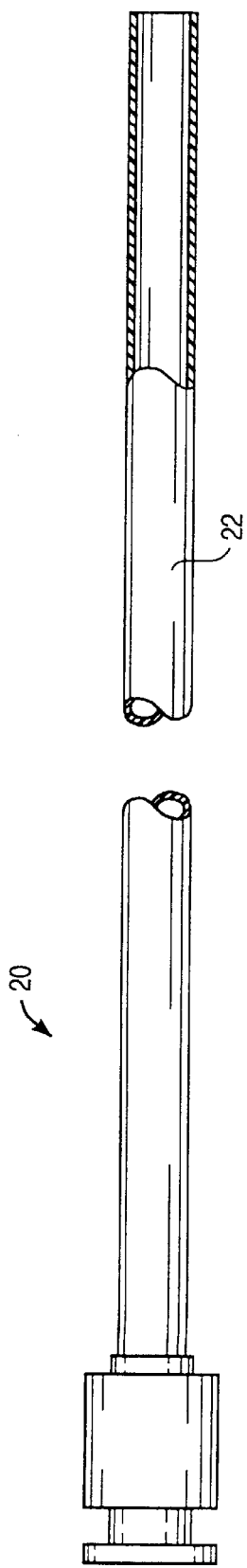
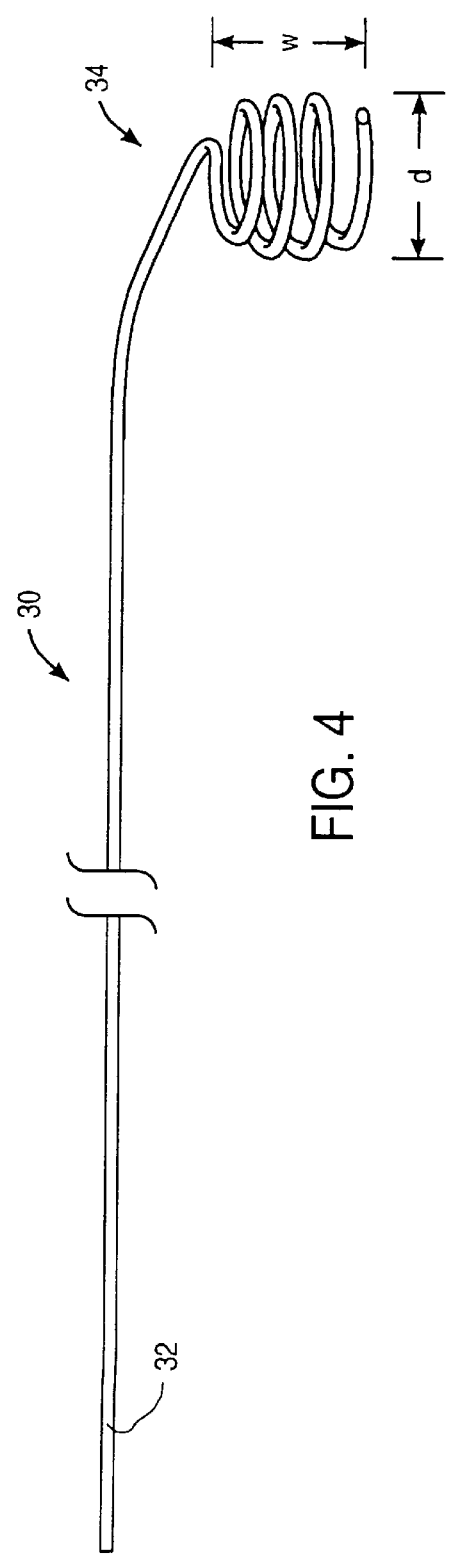
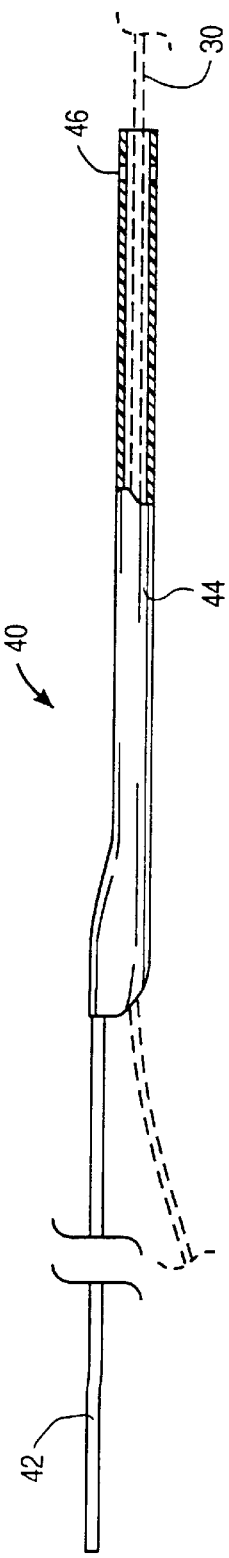
FIG. 3
FIG. 4
FIG. 5

EMBOLIC ELEMENTS AND METHODS AND APPARATUS FOR THEIR DELIVERY

This application is a continuation-in-part of application Ser. No. 08/355,142, filed on Dec. 13, 1994, now U.S. Pat. No. 5,690,671 the full disclosure of which is incorporated herein by reference.

BACKGROUND OF THE INVENTION

1. Field of the Invention

The present invention relates generally to the field of medical devices and procedures and more particularly to the structure and deployment of embolic elements for occluding target sites, such as aneurysms, within a blood vessel.

Embolic coils, also referred to as vaso-occlusion coils, are used for selectively occluding blood vessels for a variety of purposes, such as the control of internal bleeding, the occlusion of blood supply to tumors, and the blocking of blood flow to aneurysms. Of particular interest to the present invention, embolic coils may be delivered to brain aneurysms by first positioning the distal end of a small tubular catheter through an opening in the blood vessel wall to the aneurysm and then pushing a plurality of embolic coils into the aneurysm volume. The coils then occlude the aneurysm by promoting thrombus formation.

While being generally successful, such treatment methods suffer from certain deficiencies. Most embolic coils display little or no expansion when they are released from their delivery catheters. One type of coil, which achieves perhaps the best expansion ratio, is delivered through the catheter as a straightened wire filament. Upon release from the catheter, the wire assumes a preset coil configuration within the aneurysm. The resulting coil, however, does not maximize the volume occupied by the embolic device. A second common approach relies on pushing an embolic coil through a delivery catheter with the coil in its coiled configuration. As the embolic coil is released, it further deploys with a secondary helical configuration, increasing the effective width of the coil, but decreasing its length. Again, the resulting occluded volume has not been maximized.

Conventional embolic coil delivery techniques also suffer from a lack of control. In many cases, the embolic coils are pushed through the distal end of the delivery catheter and released without any control over their positioning. While certain improvements have been proposed, such as where the embolic coil is attached to a pusher wire and released from the wire only after some positioning of the coil within the aneurysm, the control over positioning is quite limited.

It would therefore be desirable to provide improved embolic element structures and methods and apparatus for their delivery and deployment. In particular, it would be desirable to provide embolic element structures which possess both a compact delivery configuration and a maximally expanded released configuration in order to increase the occlusive volume of the element. It would be further desirable to provide embolic element delivery systems and methods which can control placement and positioning of the embolic element within a blood vessel target site, such as an aneurysm, prior to release of the embolic element into the site. It would be particularly desirable if the embolic element could be deployed in a preselected three-dimensional configuration prior to release into the site.

2. Description of the Background Art

Embolic coils and catheter delivery systems for such coils are described in U.S. Pat. Nos. 4,994,069; 5,108,407; 5,122, 136; 5,217,484; 5,226,911; 5,234,437; 5,250,071; 5,261,916; and 5,312,415; and PCT applications WO 93/06503; WO 93/06884; WO 94/09705; WO 94/10936; and WO 94/11051. Endovascular placement of vascular appliances composed of shape memory materials is described in U.S. Pat. Nos. 3,868,956; 4,170,990; 4,503,569; 4,512,338; 4,950,258; and 5,067,957. The '956 patent described the in situ heating of vascular stents and filters to expand and anchor the devices within a blood vessel. Micro catheters and guidewires are described in U.S. Pat. Nos. 4,739,768; 4,813,934; 4,884,579; and 5,109,867.

SUMMARY OF THE INVENTION

The present invention provides improved embolic elements and systems and methods for their delivery and deployment within a blood vessel for selective occlusion of a target site. The embolic elements have a very compact unexpanded configuration for delivery through or over a catheter and can be expanded to a much larger size to maximize the resulting occlusion volume. The delivery system and method permit pre-positioning of the embolic element within a predefined volume prior to release of the element into the target site.

According to the present invention, the embolic element comprises a filament composed of a shape memory material, where the filament is disposed in an unexpanded configuration at a first temperature at or below a transition temperature and assumes an expanded configuration when the temperature is raised to or above the transition temperature. Preferably, the unexpanded configuration will be a tightly-wound coil which minimizes the size of the embolic element for delivery through a catheter, as described in more detail below. The expanded configuration is preferably a random matrix where the filament uncoils to define a peripheral envelope which is larger in all dimensions than that of the coil or other unexpanded configuration. In particular, the peripheral envelope will have no transverse dimension which is less than the maximum dimension of the unexpanded embolic element, typically the length of the coil prior to expansion.

According to another aspect of the present invention, a system for selectively occluding a target location within a blood vessel comprises a catheter and an embolic element as described above. The catheter includes means for heating the embolic element to or above the transition temperature when the element is positioned at the target location. The heating means may be electric, radiative, or fluid, with the preferred heating means comprising a lumen in the catheter for directing a heated medium past the embolic coil when positioned at the target location.

In a preferred aspect of the present invention, the delivery catheter has a tubular body with an axial lumen which receives the embolic element in its unexpanded configuration. The system further comprises a delivery wire having a helical section at its distal end. The embolic element, typically in its unexpanded coiled configuration, may be delivered over the delivery wire through the axial lumen of the delivery catheter. The helical section at the distal end of delivery catheter may be disposed within the target location, typically inside an aneurysm, so that the embolic element assumes the helical configuration prior to expansion and release from the catheter. In this way, positioning of the embolic element prior to release can be controlled. Additionally, by properly selecting the dimensions of the helical portion of the delivery wire, the expanded volume of the embolic element can be maximized.

In another preferred aspect of the present invention, the delivery wire of the delivery catheter comprises a selectively deployable gate at its distal end. The gate is intended to block premature or other unintended release of the embolic element from the delivery wire. The gate can be selectively "opened" when delivery is intended. Usually, the gate will be deployable between an expanded configuration that blocks passage of an embolic coil over the distal end of the wire in a non-expanded configuration which permits such passage. In an exemplary embodiment, the deployable gate is composed of a shape memory alloy which is formed into an expanded configuration which is retained at body temperature and which assumes its non-expanded configuration when exposed to an environment heated above body temperature, typically by exposure to heated saline from the catheter. In the specifically illustrated embodiment, the gate is a slotted tube formed from, e.g., Nitinol®, where the slotted region is deformed into an expanded malecott-type structure and which assumes its narrow-diameter, straightened configuration when forced back into the austenitic phase by exposure to heated saline above body temperature.

According to a first method of the present invention, an embolic element is delivered to a target site within a blood vessel by first positioning a delivery wire through a guide catheter so that a distal end of the delivery wire is disposed at the target site. The embolic element is then introduced over the delivery wire to the target site in an unexpanded configuration. The embolic element is expanded and released from the delivery wire at the target site by heating to a temperature above the transition temperature of the shape memory alloy. Such heating can be effected either by raising the temperature of the embolic element over body temperature (where the transition temperature exceeds body temperature) or by initially cooling the element below body temperature (where body temperature is at or above the transition temperature). Preferably, the delivery wire has a helix formed at its distal end so that the embolic element will assume a helical configuration prior to expansion and release at the target site.

According to a second method of the present invention, a target location in a blood vessel is occluded by introducing an embolic element composed of a shape memory alloy at the target location. The embolic element is heated above a transition temperature to cause expansion, and the target location is occluded by thrombus formation within the expanded volume of the embolic element. The target location is preferably an aneurysm and the embolic element is preferably delivered by the first method described above.

Optionally, the method of the present invention may comprise a further step of selectively permitting release of the embolic element from the delivery wire. In this way, retention of the embolic coil on the catheter can be assured until such time as the intentional release is desired. In the specific embodiment, the selective release step comprises exposing a heat memory alloy gate which blocks release of the coil to a temperature above body temperature, wherein the gate reconfigures from an expanded configuration which blocks passage of the element to a non-expanded configuration which permits passage of the element. Conveniently, the selective release may be effected by the infusion of a heated saline, typically in the same step which effects reconfiguration of the embolic coil as described above.

BRIEF DESCRIPTION OF THE DRAWINGS

FIG. 3 is an elevational view of a guide catheter used for introducing the embolic element of FIG. 1, shown in partial cross-section.

FIG. 4 is a perspective view of a delivery wire which may be used in combination with the guide catheter of FIG. 3 for introducing the embolic element of FIG. 1 according to the method of the present invention.

FIG. 5 is a coil pusher which may be used to advance the embolic element over the delivery wire of FIG. 4.

DESCRIPTION OF THE PREFERRED EMBODIMENT

The embolic element of the present invention is composed of a shape memory material, usually a shape memory metal alloy such as nickel-titanium alloy, available under the tradename Nitinol®. Alternatively, the embolic elements may be composed of shape memory plastics, such as homo- or copolymers of lactide and/or glycolide, as described in U.S. Pat. No. 4,950,258, the full disclosure of which is incorporated herein by reference. The embolic element will have an unexpanded configuration below a transition temperature (which is characteristic of the particular shape memory material utilized) and an expanded configuration which is attained when the element is exposed to a temperature at or above the transition temperature. The element may be delivered to the target site within a blood vessel in its unexpanded (compact) configuration and thereafter transformed to its expanded configuration in order to increase the occlusive volume provided by the element after release at the target site. The embolic element will be delivered to the target site at a temperature below the transition temperature, (typically being body temperature but optionally being a temperature below body temperature) and will be selectively transformed to the expanded configuration after release at the target site by exposure to a temperature at or above the transition temperature. Usually, the temperature change will be effected by heating the embolic element above body temperature, as will be the case when the element is delivered to the target site at body temperature. Alternatively, body temperature may be sufficient to effect expansion when the element is delivered to the target site at a temperature below body temperature.

In a preferred aspect of the present invention, the embolic element is a filament composed of a metal or plastic (polymeric) shape memory material having a diameter in the range from 0.01 mm to 0.1 mm, preferably from 0.02 mm to 0.05 mm, and a length in the range from about 30 cm to 1000 cm, preferably from 90 cm to 300 cm. In the unexpanded configuration of the embolic element, the filament is formed into a tightly-wound coil, typically having a diameter in the range from 0.1 mm to 1 mm, preferably from 0.25 mm to 0.5 mm, and a length in the range from 2 mm to 60 cm, preferably from 25 mm to 15 cm. The coil will usually have from 20 turns to 60,000 turns, usually from 1000 turns to 6000 turns. In the expanded configuration of the embolic element, the filament opens into a random matrix or structure having a peripheral envelope which is larger in all dimensions than the maximum dimension of the initial coiled configuration. Usually, the peripheral envelope will have a minimum width passing through the center of the random matrix in the range from 2 mm to 100 mm.

Figure 2:
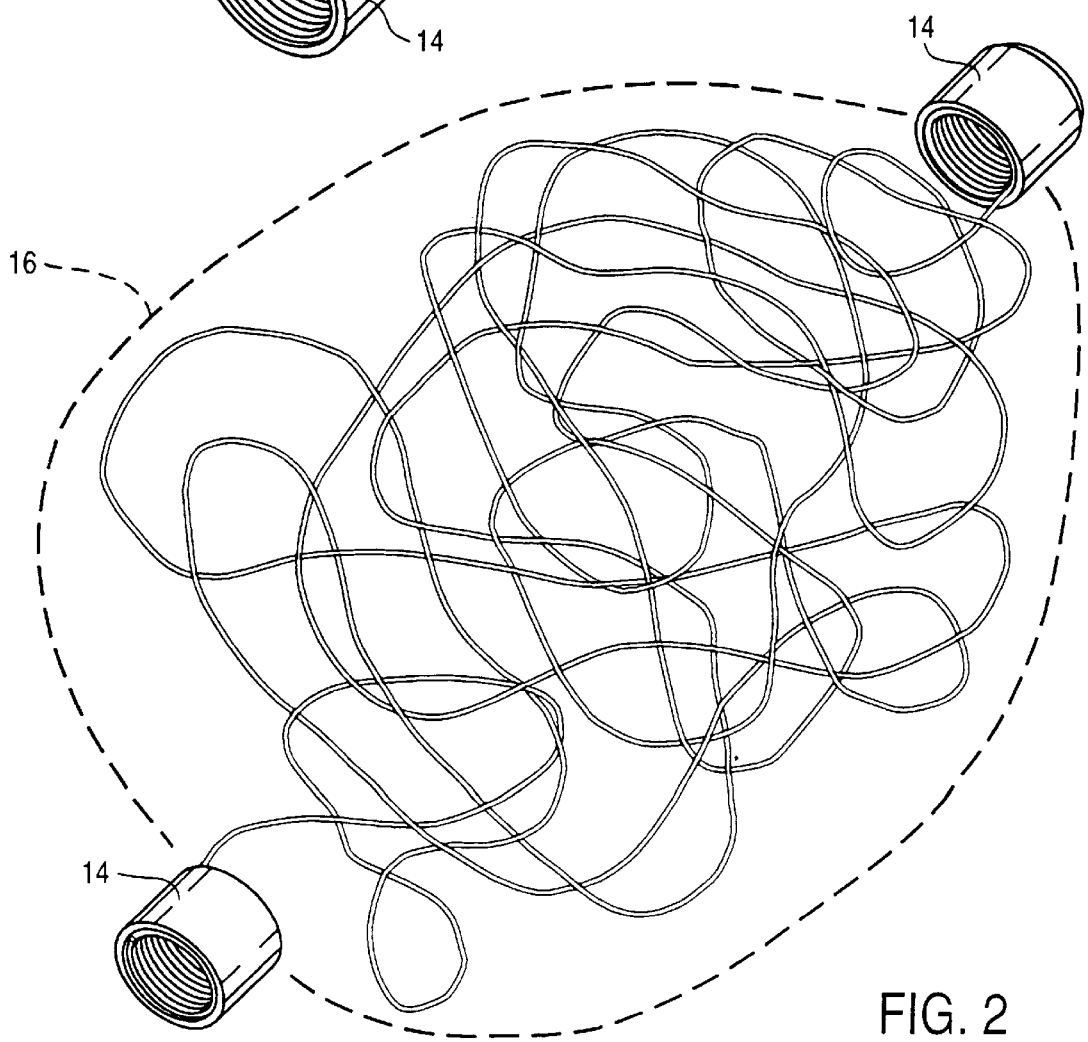
FIG. 2 is a perspective view of the embolic element of FIG. 1 shown in its expanded configuration.

A preferred metal shape memory filament is a nickel titanium wire having the diameter and length described above such wires may be obtained from a number of commercial sources, including Raychem Corporation, Menlo Park, Calif. The wires may then be formed into the preferred coil/random matrix geometry by conventional techniques. For example, the random matrix shape (as illustrated in FIG. 2 discussed below) may be permanently set into the wire by heating the wire while maintained in the desired configuration. To achieve the desired initial set, the wire should be heated to a temperature of about 500° C. for a time in the range from about 5 minutes to 60 minutes. After cooling, the wire filament may then be wound and deformed plastically to the desired coil configuration. The coil configuration will be maintained at room temperature, with transformation back to the random matrix configuration being achieved by heating the coil to a temperature above about 20° C. (the transition temperature will usually be in the range from 20° C. to 70° C.), whereby the coil will "recover" its initial random shape. Suitable shape memory plastic materials and methods for forming such materials into unexpanded and expanded configurations are described in U.S. Pat. No. 4,950,258, the full disclosure of which has previously been incorporated herein by reference.

As most shape memory materials are not radiopaque, a separate radiopaque element or member will frequently be attached to the shape memory portion of the element described above. The radiopaque element or member may have any size or configuration which is readily apparent under fluoroscopic imaging and which is compatible with introduction and use of the embolic element. For example, in the case of the unexpanded coil configuration of the embolic element, the radiopaque member will conveniently be a separate ring member attached to at least one end of the coil, and typically being composed of platinum, gold, silver, tungsten, or other radiopaque material. Use of radiopaque ring is particularly compatible with introduction of the embolic element over delivery wire, as described in more detail hereinbelow.

For other modes of delivery, the radiopaque element or member can take other forms, for example, being mounted inside of the coil or elsewhere.

In many cases, it will be desirable to modify the embolic element in some way in order to enhance its thrombogenicity. For example, components composed of highly thrombogenic materials can be secured to the embolic element. Such components include threads, nets, foams, coatings, surface texturing, studs, projections, and any other structural feature that increases the thrombogenicity and/or surface area of the embolic element. Suitable thrombogenic materials include polyester, silk, ionomer (ethylene-vinyl copolymer), collagen, albumin, and the like. Particular examples include short silk or polyester threads tied at spaced-apart intervals along the length of the filament, a silk or polyester net disposed over the peripheral envelope defined by the expanded embolic element, an open cell foam within or over the matrix defined by the expanded embolic element, a collagen or other coating over the filament surface, and the like.

The embolic element may be delivered by any one of a variety of techniques employed for the delivery of known embolic coils, including those described in U.S. Pat. Nos. 4,994,069; 5,108,407; 5,122,136; 5,217,484; 5,226,911; 5,234,437; 5,250,071; 5,261,916; and 5,312,415, the full disclosures of which are incorporated herein by reference. In some cases, it may be necessary to adapt or modify the construction of the embolic element to be compatible with the known delivery systems, for example, by including an anchor or a latch member at either or both ends of the embolic element to facilitate delivery.

A preferred delivery method and system according to the present invention employs a tubular guide catheter and a delivery wire, where the coil configuration of the embolic element may be pushed over the delivery wire through an axial lumen of the guide catheter to the target site. After release at the target site, the embolic element will be heated to or above the transition temperature in order to effect memory expansion to maximize the occlusive volume. In a particularly preferred aspect of the present invention, the delivery wire will have a helical section at its distal end. Typically, the helical section will include from 1 turn to 10 turns, preferably from 3 turns to 7 turns, with a diameter (d in FIG. 4) in the range from 2 mm to 20 mm, preferably 3 mm to 7 mm, and a width (w in FIG. 4) in the range from 1 mm to 20 mm, preferably to 3 mm to 7 mm. The helical section of the delivery wire will be disposed within the target site, typically within the target aneurysm, prior to advancement of the embolic element. The delivery wire will typically have an outside diameter in the range from about 0.25 mm to 1 mm, and a length in the range from about 60 cm to 300 cm. Typically, the distal-most 5 cm will be formed into the coil having the dimensions described above. As the embolic element is advanced over the helical section, it will assume a secondary helical or coiled configuration which matches that of the guidewire. The position of the embolic element can thus be confirmed within the target location prior to release. Moreover, inducing the secondary coiled configuration into the embolic element prior to release helps maximize the volume of the fully-extended element after heating.

After the releasing and heating of the embolic element, the delivery wire can be withdrawn back into the lumen of the guide catheter in order to disengage the expanded embolic element. The delivery catheter can be reinserted into the target location, however, in order to deliver a sufficient number of additional embolic elements in order to completely fill the target site. The guide catheter will be a small diameter tubular catheter having an axial lumen to permit introduction of the embolic element therethrough. Suitable tubular catheters for use as guide catheters according to the present invention are described in copending Application Ser. No. 08/151,320, filed on Nov. 12, 1993 now abandoned, the full disclosure of which is incorporated herein by reference. The guide catheter will typically have a length in the range from about 50 cm to 200 cm and an internal lumen having a diameter in the range from about 0.3 mm to 3 mm.

The coil pusher will have a length in the range from about 50 cm to 300 cm, with a tracking portion formed over the distal-most 5 cm to 300 cm. The tracking portion will typically be a flexible tube, such as a polymeric tubular element, having a lumen size sufficient to be received over the delivery wire and a distal tip adapted to engage against a proximal end of the embolic coil. In the case of a coiled embolic element, the distal tip will typically be a flat face designed to engage against a flat proximal end of the coil. The proximal portion of the pusher may be a solid core pusher rod typically having a diameter in the range from about 0.2 mm to 1 mm. The delivery wire may be composed of a variety of material, including stainless steel, with the distal coil being formed from a radiopaque material, such as platinum.

The embolic element delivery system will further comprise a means for heating the embolic element during or after release of the element from the delivery wire. Conveniently, the heating means will comprise a lumen for directing a heated medium, such as heated saline or contrast medium, past the element to effect expansion, where the lumen may be provided by the central lumen of the tubular guide catheter. Systems for heated saline and other media under pressure for delivery to catheters are commercially available. Alternatively, the delivery system may incorporate other heating means, including but not limited to, electric resistance heaters, electric inductive heaters, laser radiation heaters, and the like.

Figure 1:
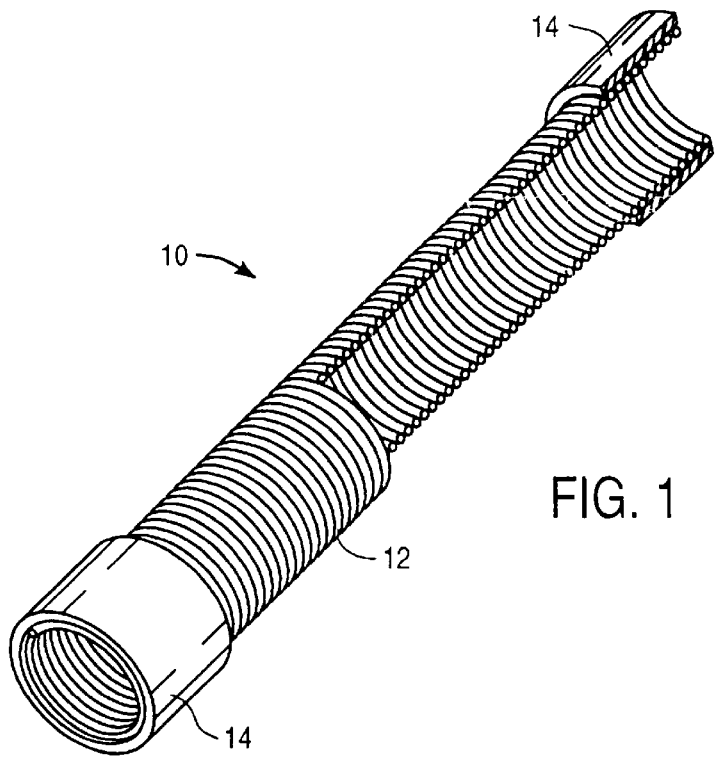
FIG. 1 is a perspective view of an embolic element constructed in accordance with the principles of the present invention, shown in its unexpanded configuration in partial cross-section.

Referring now to FIGS. 1 and 2, the structure of an exemplary embodiment of an embolic element 10 constructed in accordance with the principles of the present invention will be described. Embolic element 10 is formed as a helical coil 12 of a single wire filament composed of a shape memory alloy as discussed above. The coil includes a pair of radiopaque rings 14, one being disposed at each end of the coil. The rings may be attached to the coil using a conventional adhesive, such as an epoxy adhesive. The coil has a length of about 5 cm, an outside diameter of about 0.46 mm, and inside diameter of about 0.41 mm, where the wire filament has a diameter of about 0.025 mm and a length of about 150 cm. The embolic element 10 is shown in its unexpanded configuration in FIG. 1. After heating to above the transition temperature characteristic of the particular shape memory alloy selected, the wire filament of the coil will assume the random configuration illustrated in FIG. 2. The wire filament in its random configuration will define a peripheral envelope 16 shown in broken line in FIG. 2. The peripheral envelope generally defines the volume available for inducing thrombosis within the blood vessel after the element 10 has been deployed.

An exemplary guide catheter 20 for use in delivering the embolic element 10 is illustrated in FIG. 3. The guide catheter comprises a tubular body 22 which is optionally reinforced to enhance pushability and torqueability, as described in copending Application Ser. No. 08/151,320, the full disclosure of which has previously been incorporated herein by reference. The guide catheter has a length of about 150 cm and an inside lumen diameter of about 0.5 mm.

Delivery wire 30 is illustrated in FIG. 4. The wire comprises a proximal wire body 32 having a length of about 170 cm and a diameter of about 0.25 mm. A distal helix 34 is formed at the distal end of the wire body 32 having a width w of about 5 mm and a diameter d of about 3 mm, and the coil will include about 4 full turns.

A suitable coil pusher 40 is illustrated in FIG. 5. Coil pusher 40 includes a proximal push rod 42 comprising a solid core stainless steel wire having a diameter of about 0.25 mm and a length of about 175 cm. A distal pusher section 44 has a length of about 35 cm and an inside diameter of about 0.3 mm. The coil pusher preferably includes a radiopaque marker 46 near its distal tip. The pusher section 44 may be introduced over the delivery wire 30, as shown in broken line.

Figure 6:
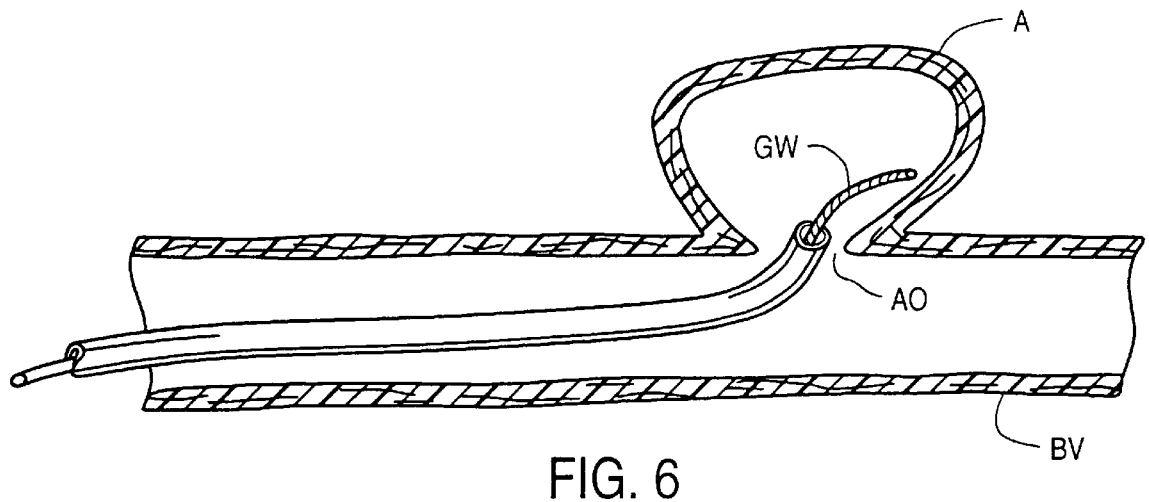
FIGS. 6–11 illustrate use of a delivery system comprising the guide catheter, delivery wire, and coil pusher for introducing the embolic element of FIG. 1 to a target site within a blood vessel.
Figure 7:
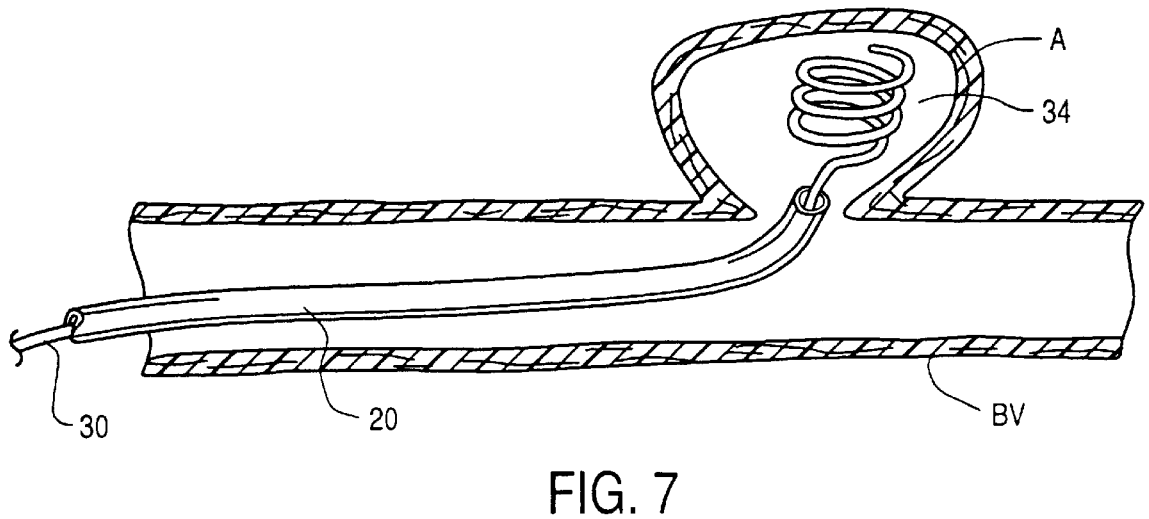
Figure 8:
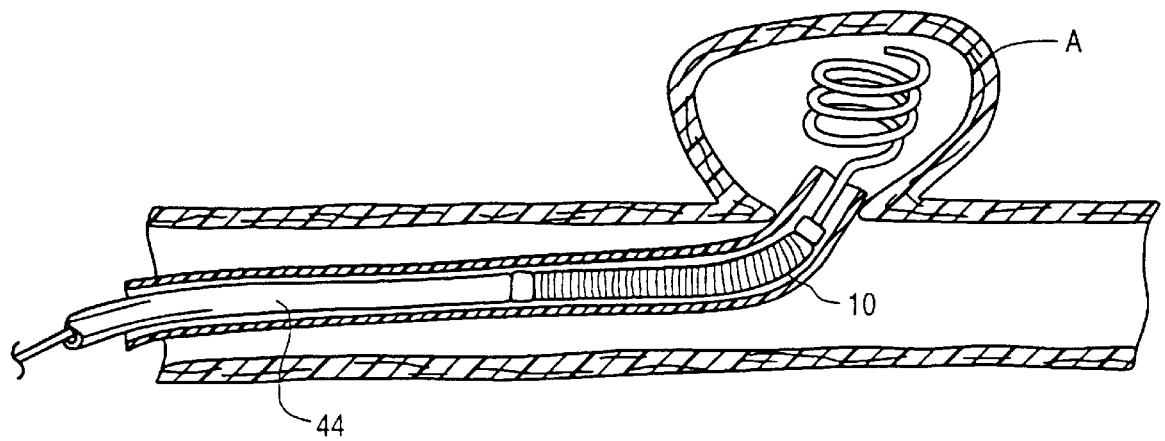
Figure 9:
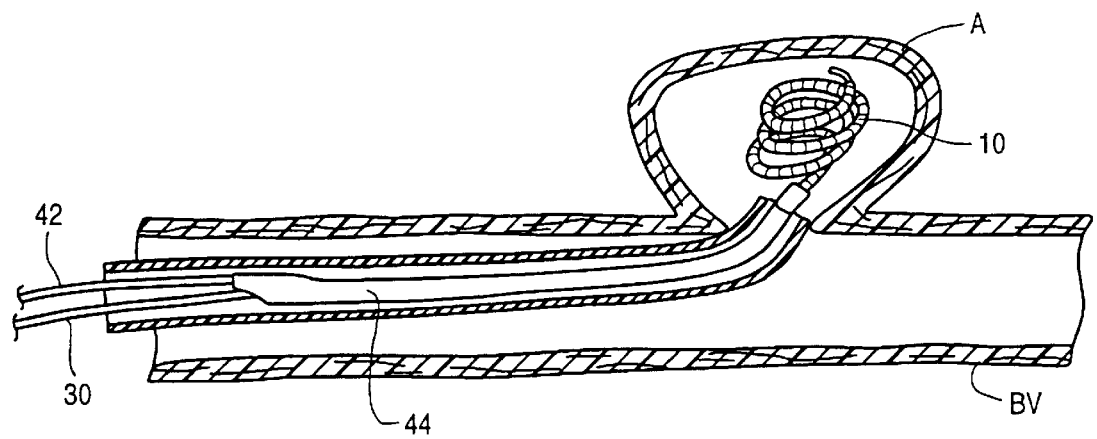
Figure 10:
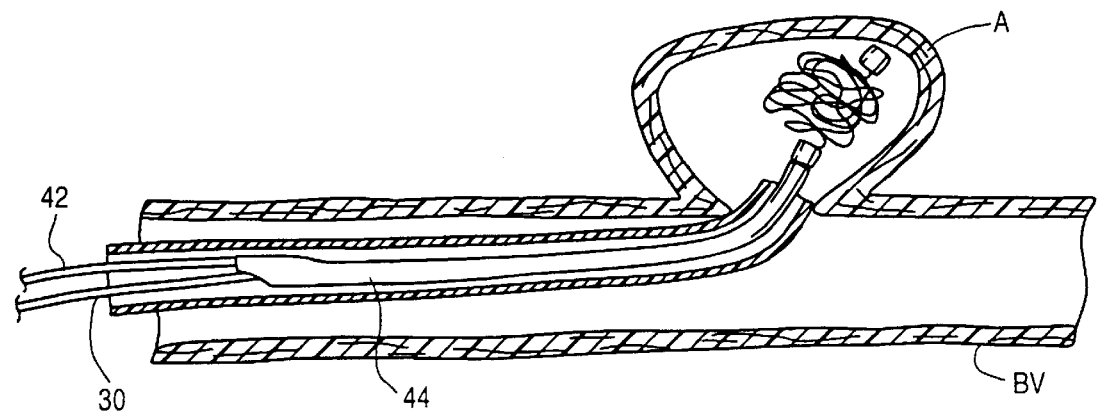
Figure 11:
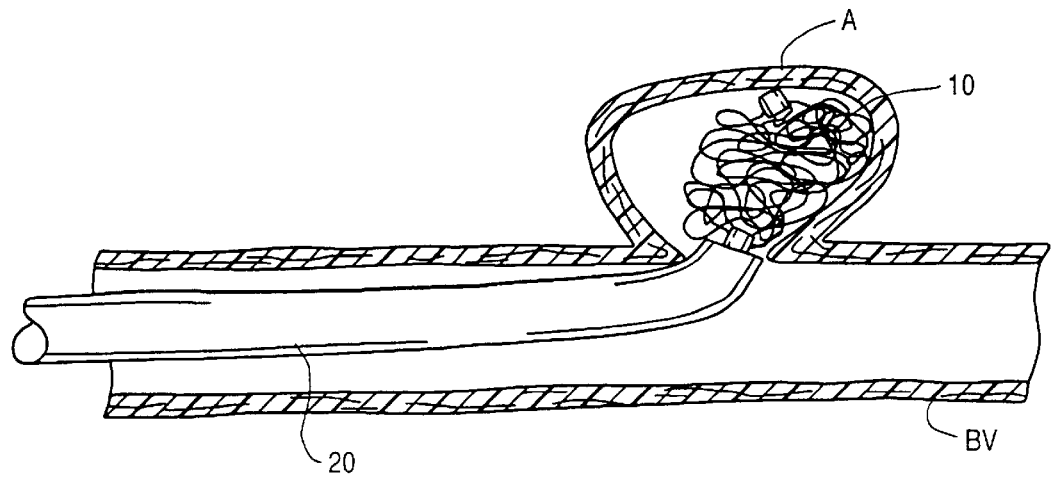

Referring now to FIGS. 6–11, use of the delivery system of the present invention to deliver the exemplary embolic element 10 to an aneurysm A in a blood vessel BV will be described. Initially, guide catheter 20 is introduced through an opening AO to the aneurysm A over a conventional guidewire GW, as shown in FIG. 6. After the guide catheter 20 is in place, the guidewire GW is withdrawn and exchanged for the delivery wire 30, as illustrated in FIG. 7. After the coil section 34 of the delivery wire 30 is fully introduced into the interior of aneurysm A, the embolic element 10 may be introduced over the delivery wire. This is done by pushing the coil 10 with the pusher section 44 of the coil pusher 42, as illustrated in FIG. 8. The coil pusher 40 is advanced sufficiently so that the embolic element 10 is transferred entirely from the axial lumen of the guide catheter 20 and into the interior volume of the aneurysm A. Embolic element 10 will assume the helical configuration of the helical section 34 of the guidewire, as illustrated in FIG. 9. A heated medium may then be introduced through the axial lumen of the guide catheter in order to effect expansion of the embolic element 10 into its expanded, random configuration, as illustrated in FIG. 10. The delivery wire 30 may then be withdrawn so that the helical section 34 is removed from the interior of the embolic element 10, allowing the embolic element 10 to achieve its fully expanded, random configuration, as illustrated in FIG. 11.

It will be appreciated that a plurality of embolic elements 10 may be required to fill and initiate thrombosis of the entire internal volume of the aneurysm A. Additional embolic elements 10 may be introduced by repeating the steps just described a sufficient number of times in order to completely fill the internal volume.

Figure 12:
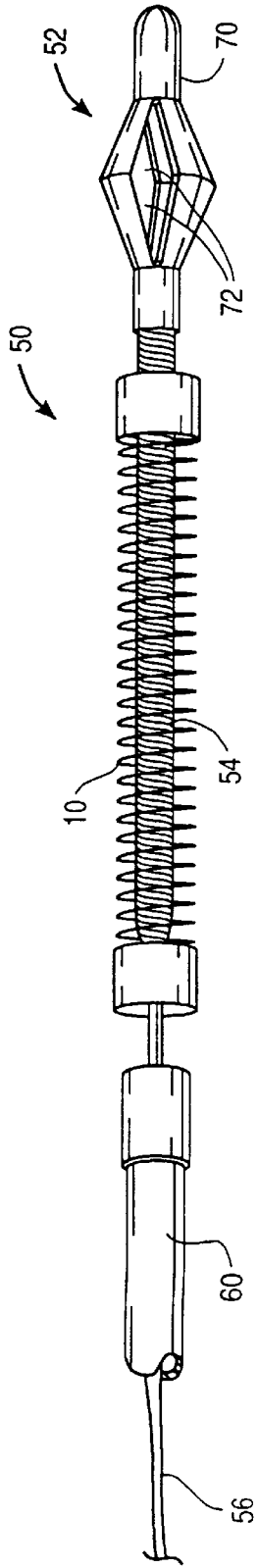
FIGS. 12–14 illustrate the construction and use of a selective delivery gate on the delivery catheter of the present invention.
Figure 13:
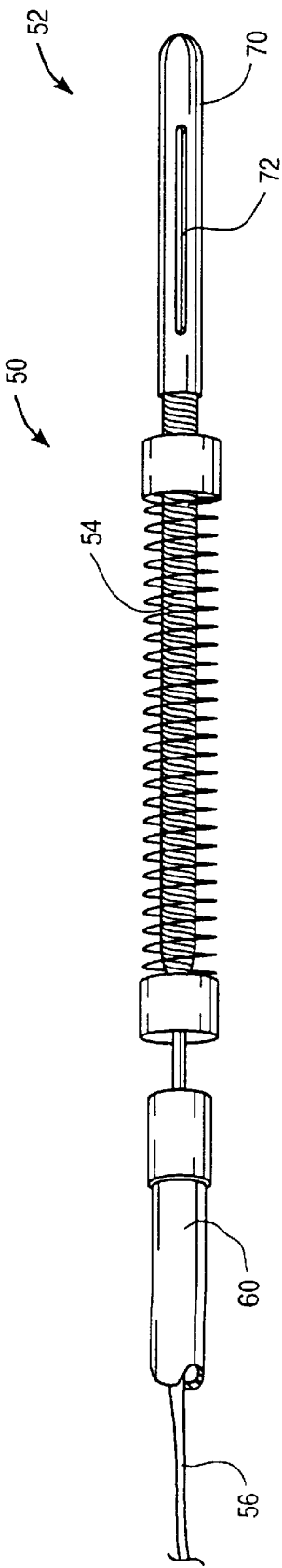
Figure 14:
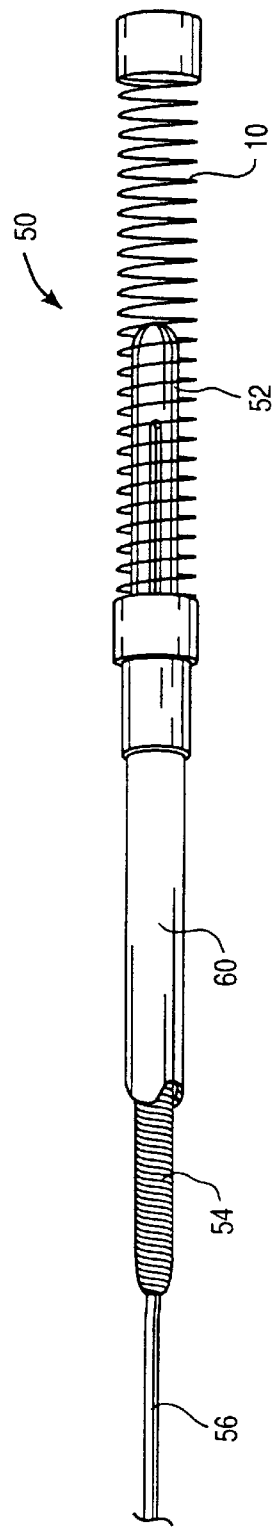

In some cases, it will be desirable to provide a mechanism on the delivery catheter for selectively blocking premature or unintended release of the embolic element 10. An exemplary delivery system 50 employing a gate 52 capable of such selective blockage is illustrated in FIGS. 12–14. The gate 52 is disposed at the distal end of a delivery coil 54 which in turn is disposed at the distal end of delivery wire 56. A coil pusher 60 is also provided, generally as described above in connection with the earlier embodiments.

The gate 52 can have a variety of specific constructions, with the primary requirement being that it is selectively reconfigurable between a blocking, e.g., expanded, configuration and a non-blocking, e.g., non-expanded, configuration. The gate 52 could be actuated or deployed in a variety of ways, including mechanically, electrically, chemically, or the like. The preferred deployment, however, will be by exposure to a temperature above body temperature, typically by exposure to heated saline in a manner similar to heating of the embolic coil itself. Such heating could also be effected by electrically heating the gate, e.g., by introducing a low power electrical current therethrough. Other mechanical systems include use of a pull wire or other constraint to allow self-contraction of a gate element, chemical dissolution of a block which is present at the distal end of the catheter, or the like.

In the illustrated embodiment, the gate comprises a tube 70 having a plurality of axial slots 72 formed therein. The tube is composed of a heat memory alloy, such as Nitinol®, with the tube initially in its straightened, non-expanded configuration, as shown in FIG. 13. The tube is then heated and/or stressed into the expanded configuration of FIG. 12 in a manner so that the tube will remain in its expanded configuration until exposed to a temperature above body temperature, typically in the range from 20° C. to 70° C., as set forth above for the embolic element. By employing both a gate 52 and embolic element 10 having substantially the same transition temperatures, it will be appreciated that the coil can be released and selectively transformed to its expanded configuration using the same delivery step for the heated saline. Note that the system 50 of FIGS. 12–14 will also include an outer catheter sheath similar to the guide catheter 20 illustrated in FIG. 3. Thus, the heated saline or other medium can be introduced through the lumen of the guide catheter (not shown).

As illustrated in FIGS. 12–13, deployment of the embolic element 10 may be accomplished essentially as illustrated in FIGS. 6–11, with the following difference: after the distal end of the delivery catheter is located at the desired target site, the heated medium will be introduced, causing both the contraction of the gate 52, as shown in FIG. 13, and the expansion of the embolic coil 10. The coil 10 can then be disengaged by advancing the coil pusher 60 in a forward direction, as illustrated in FIG. 14. Note, in FIGS. 12–14, the delivery coil 54 is shown to a have a relatively short length, only slightly longer than the embolic coil 10. The delivery coil 54, however, can readily be constructed to have a longer length, and also to have a coiled configuration, generally as shown and described regarding helix 34 of delivery wire 30 in FIG. 4.

Although the foregoing invention has been described in some detail by way of illustration and example, for purposes of clarity of understanding, it will be obvious that certain changes and modifications may be practiced within the scope of the appended claims.

What is claimed is:

1. An embolic element comprising a filament composed of a shape memory material having a transition temperature, wherein the filament is in an unexpanded coiled configuration at a first temperature at or below the transition temperature and assumes an expanded configuration when the temperature is raised to or above the transition temperature.

2. An embolic element as in claim 1, wherein the shape memory material is selected from the group consisting of a nickel titanium alloy having a transition temperature in the range from 20° C. to 70° C. and a plastic shape memory material.

3. An embolic coil as in claim 1, further comprising a radiopaque segment attached to the wire filament.

4. An embolic coil as in claim 3, wherein the unexpanded configuration is a coil and wherein the radiopaque segment is a ring attached to at least one end of the coil, wherein the ring has a diameter which is substantially equal to that of the coil.

5. An embolic element as in claim 1, further comprising a thrombogenic component secured to the filament.

6. A system for selective occlusion of a target location within a blood vessel, said system comprising
  a catheter having an axial lumen;
  a delivery wire having a helical distal end, wherein the delivery wire may be positioned within the axial lumen of the catheter to provide an introducing path for the embolic element wherein the delivery wire has a selectively deployable gate at its distal end;
  an embolic element composed of a shape memory alloy having a transition temperature, an unexpanded configuration below the transition temperature sized to fit within or over the catheter, and an unexpanded configuration above the transition temperature which defines a peripheral envelope which is larger in all dimensions than that of the unexpanded configuration wherein the unexpanded configuration of the embolic element is a coil, wherein the coil may be coaxially passed over the delivery wire and through the axial lumen of the catheter; and
  means on the catheter for heating the embolic element to the transition temperature when the element is positioned at the target location.

7. A system as in claim 6, wherein the catheter comprises a tubular body having an axial lumen which receives the embolic element in its unexpanded configuration therethrough.

8. A system as in claim 6, wherein the coil is formed from a filament having a diameter in the range from 0.01 mm to 0.1 mm and a length in the range from about 30 cm to 1000 cm, wherein the expanded coil has a diameter in the range from 0.1 mm to 1 mm and a length in the range from 2 mm to 600 mm, and wherein the peripheral envelope has a minimum dimension of in the range from 2 mm to 100 mm.

9. A system as in claim 6, wherein the coil on the delivery wire has a length in the range from 1 mm to 20 mm, a diameter in the range from 2 mm to 20 mm, and consists of from 1 turn to 10 turns.

10. A system as in claim 6, wherein the gate is deployable between an expanded configuration that blocks passage of embolic coil over the distal end of the wire and a non-expanded configuration which permits passage.

11. A system as in claim 10, wherein the deployable gate is composed of a heat memory alloy that is in its expanded configuration at body temperature and which assumes its non-expanded configuration when exposed to a medium heated above body temperature.

12. A method for delivering an embolic element to a target site in a blood vessel, wherein said method comprises:
  positioning a delivery wire through a guide catheter so that a distal end of the delivery wire is disposed at the target site;
  introducing the embolic element over the delivery wire to the target site, wherein the embolic element is composed of a shape memory material and is in an unexpanded configuration which conforms to the delivery wire as the element is being introduced;
  expanding the embolic element by exposure to a temperature above the transition temperature of the shape memory alloy; and
  selectively permitting release of the embolic element from the delivery wire.

13. A method as in claim 12, wherein the embolic element is a filament having a coiled configuration prior to expansion.

14. A method as in claim 13, wherein expanding the embolic element causes the filament to assume a random configuration having a peripheral envelope which is larger in all dimensions than that of the coiled configuration.

15. A method as in claim 12, wherein the embolic element is introduced over a helix formed at the distal end of the delivery wire, wherein the embolic element assumes a helical configuration defined by the delivery wire prior to expansion.

16. A method as in claim 12, wherein the embolic element is expanded by flushing a heated liquid medium through the guide catheter and past the embolic element at the target site.

17. A method as in claim 12, wherein the selectively permitting step comprises exposing a heat memory alloy gate to a temperature above body temperature, wherein the gate reconfigures from an expanded configuration which blocks passage of the element over the distal end of the delivery wire to a non-expanded configuration which permits passage of the element over the distal end of the delivery wire.

18. A method for occluding a target location in a blood vessel, said method comprising
  introducing an embolic element composed of a shape memory alloy at the target location in an unexpanded coil configuration over a delivery wire;

heating the embolic element above a transition temperature to cause expansion of the element to an expanded configuration; and selectively permitting release of the embolic element from the delivery wire wherein thrombus forms in the expanded embolic matrix to occlude at least a portion of the target location in the blood vessel.

19. A method as in claim 18, wherein the target location is an aneurysm.

20. A method as in claim 18, wherein the delivery wire has a helical distal tip disposed in the target location, wherein the coiled embolic element assumes a helical configuration as it travels over the distal helix of the delivery wire.

21. A method as in claim 18, wherein the expanded configuration of the embolic element defines a peripheral envelope which is larger in all dimensions than that of the coiled configuration.

22. A method as in claim 18, wherein the embolic element is heated by flushing a heated liquid medium past the embolic element at the target site.

23. A method as in claim 18, wherein the selectively permitting step comprises exposing a heat memory alloy gate to a temperature above body temperature, wherein the gate reconfigures from an expanded configuration which blocks passage of the element over the distal end of the delivery wire to a non-expanded configuration which permits passage of the element over the distal end of the delivery wire.

* * * * *